(12) United States Patent
Choi

(10) Patent No.: US 11,678,858 B2
(45) Date of Patent: Jun. 20, 2023

(54) ULTRASONIC DIAGNOSTIC APPARATUS AND METHOD FOR CONTROLLING ULTRASONIC SCAN USING ECG GATING

(71) Applicant: CANON MEDICAL SYSTEMS CORPORATION, Otawara (JP)

(72) Inventor: Jaeho Choi, Utsunomiya (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 31 days.

(21) Appl. No.: 16/397,291

(22) Filed: Apr. 29, 2019

(65) Prior Publication Data
US 2019/0343481 A1    Nov. 14, 2019

(30) Foreign Application Priority Data

May 8, 2018  (JP) .............................. JP2018-089849
Apr. 19, 2019  (JP) .............................. JP2019-079747

(51) Int. Cl.
*A61B 8/08*    (2006.01)
*A61B 8/06*    (2006.01)
*A61B 8/00*    (2006.01)

(52) U.S. Cl.
CPC ............ *A61B 8/0883* (2013.01); *A61B 8/065* (2013.01); *A61B 8/488* (2013.01); *A61B 8/5207* (2013.01);
(Continued)

(58) Field of Classification Search
CPC ....... A61B 8/0883; A61B 8/065; A61B 8/488; A61B 8/5207; A61B 8/4444; A61B 8/4488; A61B 8/543; A61B 5/352
See application file for complete search history.

(56) References Cited

U.S. PATENT DOCUMENTS 6,210,333 B1 *  4/2001  Gardner ................. A61B 8/481
                                                            600/450
6,288,541 B1 *  9/2001  Dumoulin ........ G01R 33/56308
                                                            324/306
(Continued)

FOREIGN PATENT DOCUMENTS

JP    2006-507907         3/2006
JP    2011072448 A *    4/2011
(Continued)

OTHER PUBLICATIONS

Translation of JP 2011072448 (Year: 2011).*
(Continued)

*Primary Examiner* — Joel Lamprecht
*Assistant Examiner* — Nyrobi Celestine
(74) *Attorney, Agent, or Firm* — Oblon, McClelland, Maier & Neustadt, L.L.P.

(57) ABSTRACT

The ultrasonic diagnostic apparatus according to a present embodiment includes processing circuitry. The processing circuitry is configured to: detect, based on an electrocardiogram signal, a specific heart phase in a former heartbeat and a specific heart phase in a latter heartbeat thereafter; sequentially calculate a delay time from the specific heart phase in the latter heartbeat based on a time interval between the specific heart phase in the former heartbeat and the specific heart phase in the latter heartbeat, and control an ultrasonic probe to initiate an ultrasonic scan at a timing when the sequentially calculated delay time is elapsed from the specific heart phase in the latter heartbeat.

5 Claims, 11 Drawing Sheets

(52) U.S. Cl.
CPC ........... *A61B 8/4444* (2013.01); *A61B 8/4488* (2013.01); *A61B 8/543* (2013.01)

(56) References Cited

U.S. PATENT DOCUMENTS

| | | |
|---|---|---|
| 9,924,928 B2 | 3/2018 | Choi et al. |
| 2006/0155192 A1 | 7/2006 | Bendiksen et al. |
| 2007/0078344 A1* | 4/2007 | Rafter ................. G01S 7/52041 600/450 |
| 2010/0249574 A1* | 9/2010 | Miyazaki ............. A61B 5/7285 600/413 |
| 2015/0025337 A1* | 1/2015 | Choi ...................... A61B 8/543 600/301 |
| 2015/0139388 A1* | 5/2015 | Liu ........................ A61B 6/541 378/62 |
| 2015/0223782 A1* | 8/2015 | Yamagata ............ A61B 8/4461 600/462 |
| 2015/0366473 A1* | 12/2015 | Shimuta ................. A61B 5/349 600/479 |

FOREIGN PATENT DOCUMENTS

| | | |
|---|---|---|
| JP | 2011-234863 A | 11/2011 |
| JP | 2013-233419 | 11/2013 |
| JP | 2013-233419 A | 11/2013 |
| JP | 2016-172008 | 9/2016 |

OTHER PUBLICATIONS

Becker, Christoph R., et al. Multi-slice and Dual-source CT in Cardiac Imaging: Principles—Protocols—Indications—Outlook. Germany, Physica-Verlag, 2006. (Year: 2006).*

Yasushi Orihashi, "Study Design and Statistical Evaluation of QT Prolongation", Jpn J Biomet vol. 29, Special Issue 1, 2008, 8 pages.

* cited by examiner

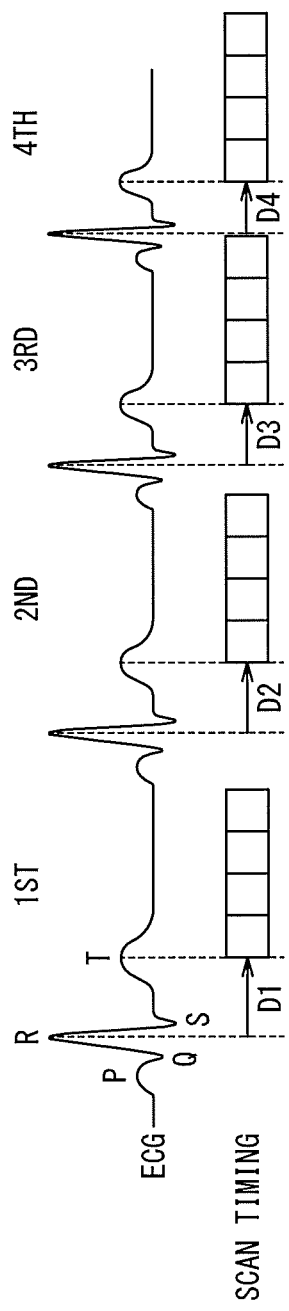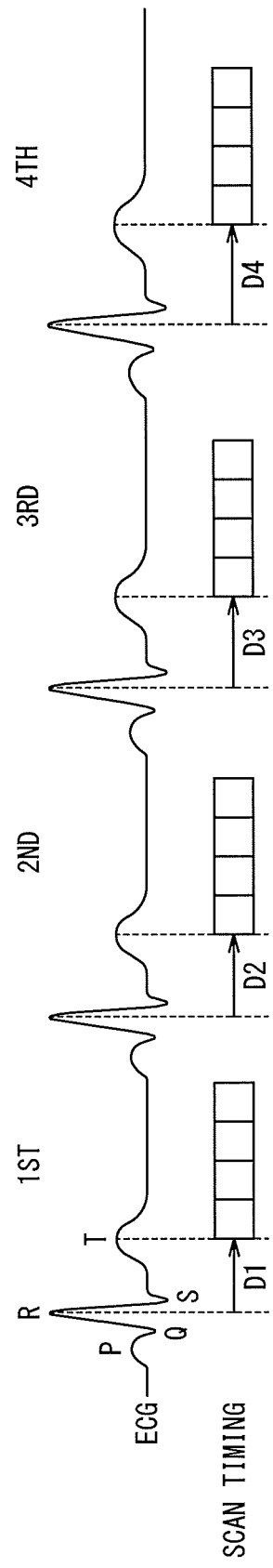

| RRs [ms] | Tds [ms] |
|---|---|
| 1500 | 400 |
| RR [ms] | Tdc [ms] |
| 1000 | 323 |
| 1010 | 325 |
| 1020 | 326 |
| 1030 | 328 |
| 1040 | 329 |
| 1050 | 331 |
| 1100 | 338 |
| 1200 | 354 |
| 1300 | 369 |
| 1400 | 358 |
| 1500 | 400 |
| 2000 | 477 |
| 990 | 321 |
| 980 | 320 |
| 970 | 318 |
| 960 | 317 |
| 950 | 315 |
| 900 | 308 |
| 800 | 292 |
| 700 | 277 |
| 600 | 261 |

FIG. 7

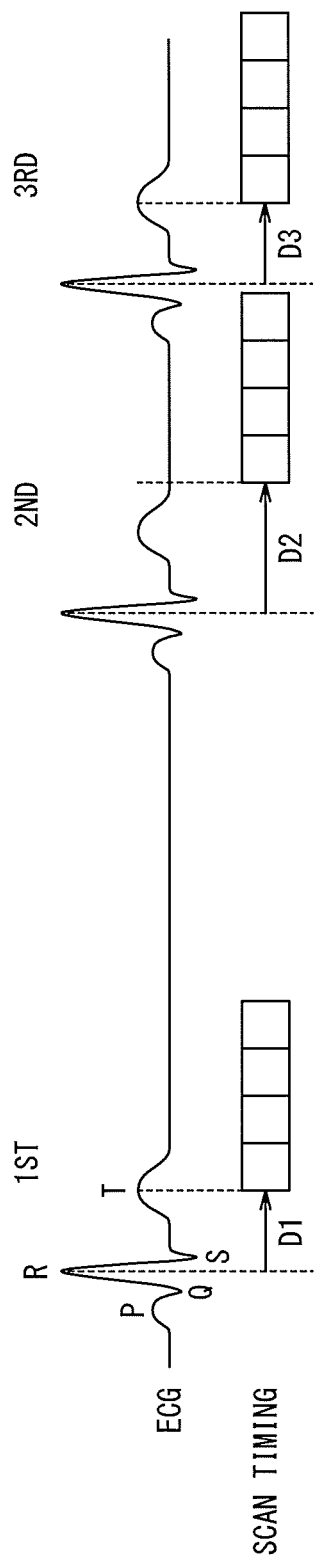
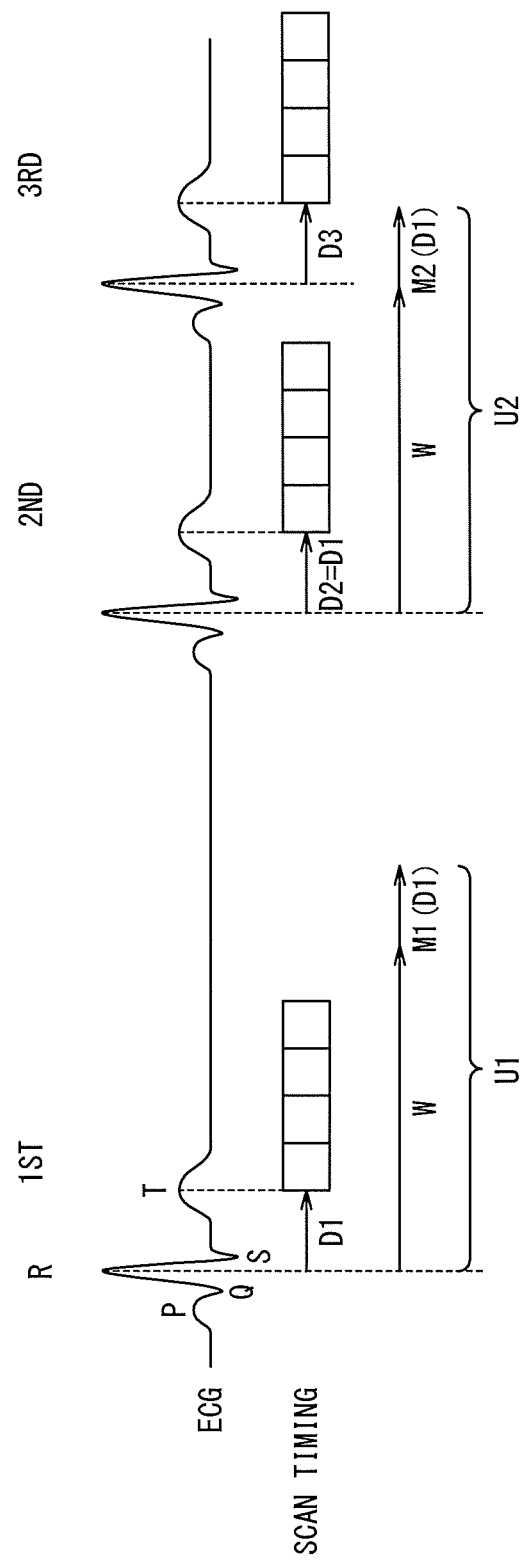
FIG. 8A
FIG. 8B

ULTRASONIC DIAGNOSTIC APPARATUS AND METHOD FOR CONTROLLING ULTRASONIC SCAN USING ECG GATING

CROSS-REFERENCE TO RELATED APPLICATION

This application is based upon and claims the benefit of priority from Japanese Patent Application No. 2018-089849, filed on May 8, 2018, and Japanese Patent Application No. 2019-079747, filed on Apr. 19, 2019, the entire contents of each of which are incorporated herein by reference.

FIELD

An embodiment as an aspect of the present invention relates to an ultrasonic diagnostic apparatus, a medical image processing apparatus, and a method for controlling an ultrasonic scan.

BACKGROUND

In the medical field, an ultrasonic diagnostic apparatus is used for imaging the inside of a subject using ultrasonic waves generated by multiple transducers (piezoelectric transducers) of an ultrasonic probe. The ultrasonic diagnostic apparatus causes the ultrasonic probe, which is connected to the ultrasonic diagnostic apparatus, to transmit ultrasonic waves into the subject, generates an echo signal based on a reflected wave, and obtains a desired ultrasonic image by image processing.

The ultrasonic diagnostic apparatus is able to detect an R-wave from the waveform of an electrocardiogram (ECG) signal output from an ECG device, and to perform an ECG gated scan synchronized with the R-wave. Specifically, the ultrasonic diagnostic apparatus is able to start a scan after a delay time from the R-wave. The delay time is set based on the initial RR interval. That is, even if the RR interval changes in heartbeats, the delay time is a fixed value.

Figure 5A:
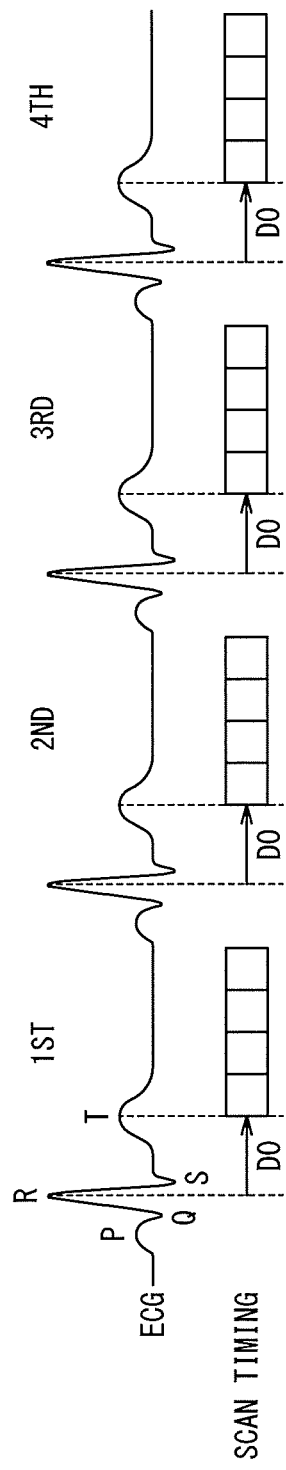
Figure 5B:
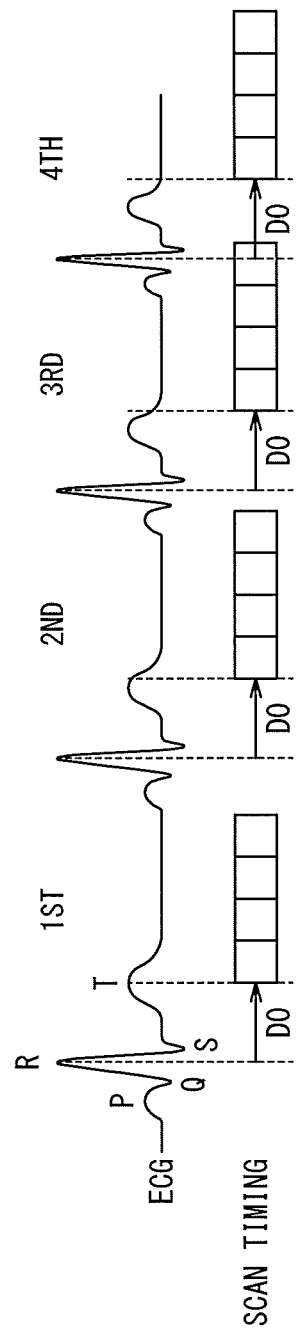
Figure 5C:
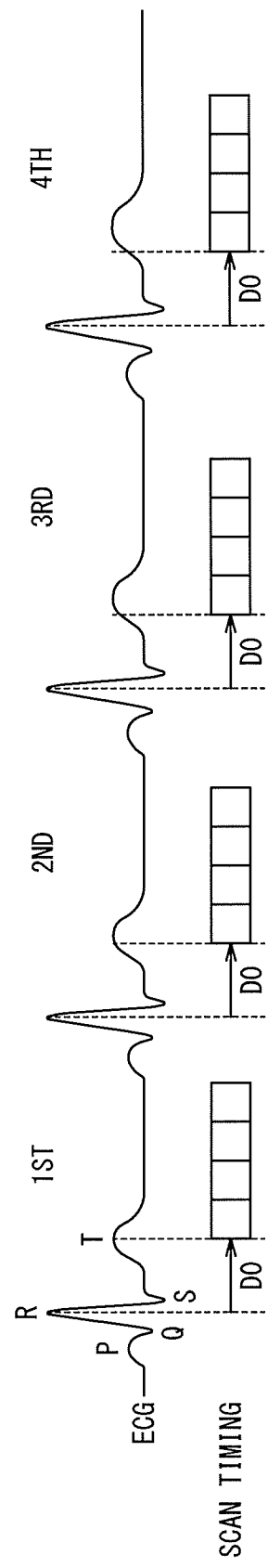

Each of FIGS. 5A to 5C is a diagram showing an ECG waveform and a scan timing when the fixed delay time is adopted.

Each of FIGS. 6A and 6B is a diagram showing an ECG waveform and a scan timing when a variable delay time is adopted in the ultrasonic diagnostic apparatus according to the first embodiment.

FIG. 7 is a table showing an example of a relationship between an RR interval and the variable delay time in the ultrasonic diagnostic apparatus according to the first embodiment.

Each of FIGS. 8A and 8B is a diagram showing an ECG waveform and a scan timing when the variable delay time is adopted in the ultrasonic diagnostic apparatus according to the first embodiment.

Figure 9:
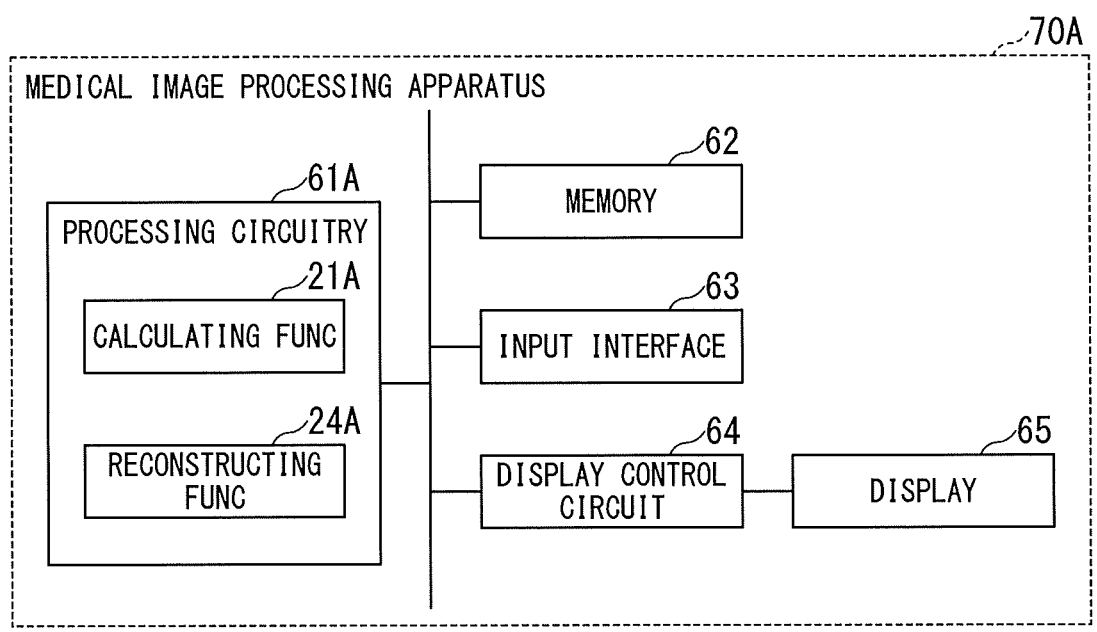

FIG. 9 is a schematic view showing a configuration of a medical image processing apparatus according to a second embodiment.

Figure 10:
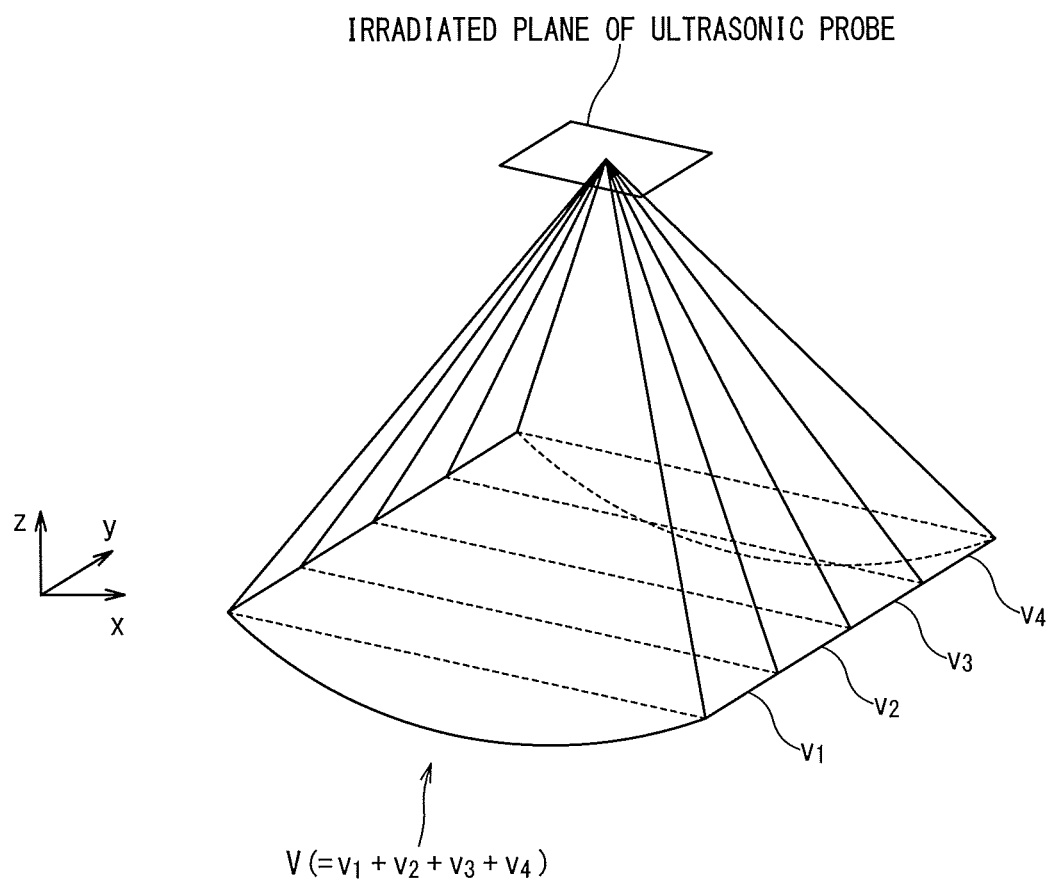

FIG. 10 is a diagram showing a relationship between multiple sub volume data and full volume data in the medical image processing apparatus according to the second embodiment.

Figure 11:
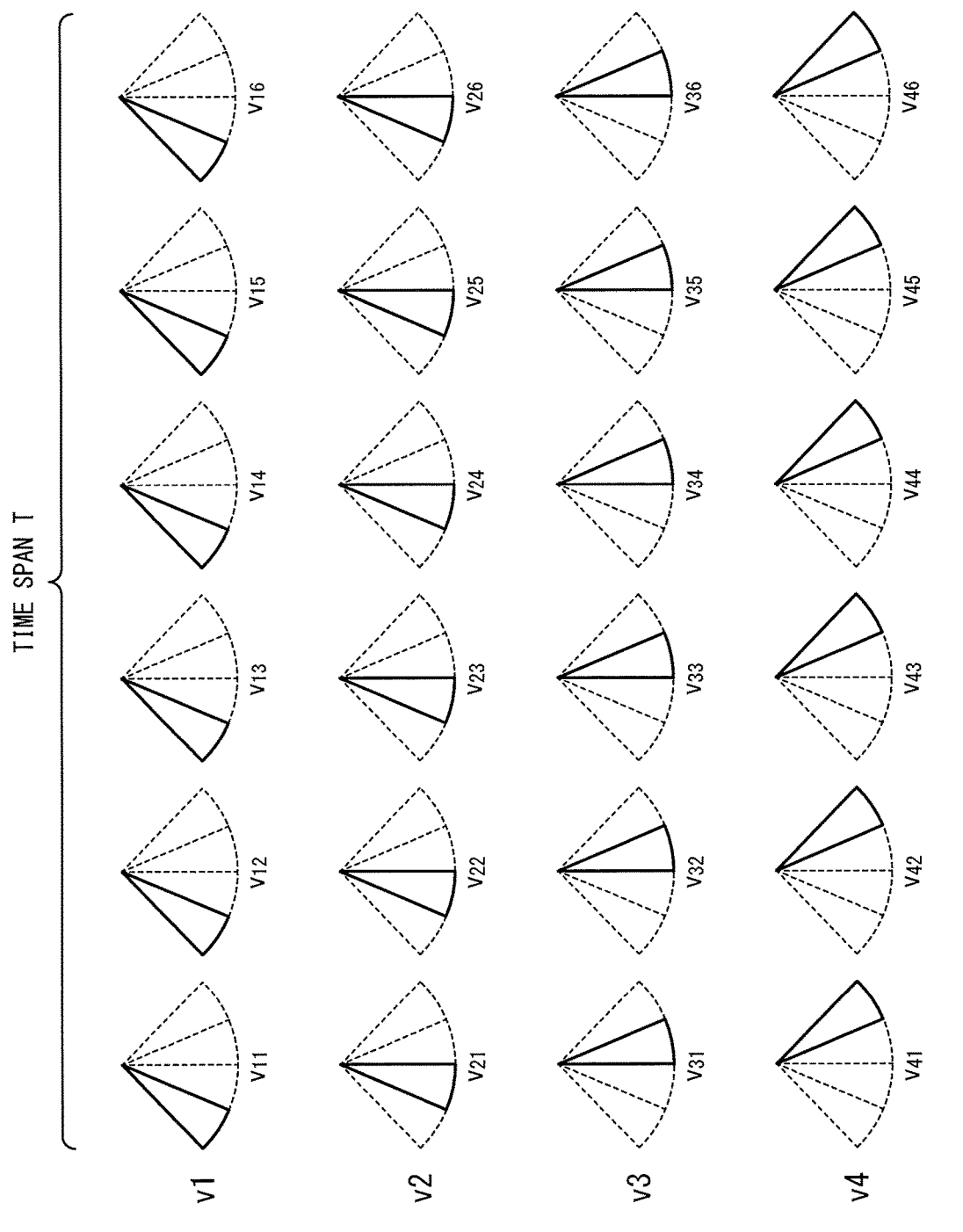

FIG. 11 is a diagram showing an example of multiple sub-volume data in the medical image processing apparatus according to the second embodiment.

DETAILED DESCRIPTION

An ultrasonic diagnostic apparatus, a medical image processing apparatus, and a method for controlling an ultrasonic scan according to a present embodiment will be described with reference to the accompanying drawings.

The ultrasonic diagnostic apparatus according to a present embodiment includes processing circuitry. The processing circuitry is configured to: detect, based on an electrocardiogram signal, a specific heart phase in a former heartbeat and a specific heart phase in a latter heartbeat thereafter; sequentially calculate a delay time from the specific heart phase in the latter heartbeat based on a time interval between the specific heart phase in the former heartbeat and the specific heart phase in the latter heartbeat, and control an ultrasonic probe to initiate an ultrasonic scan at a timing when the sequentially calculated delay time is elapsed from the specific heart phase in the latter heartbeat.

1. First Embodiment

Figure 1:
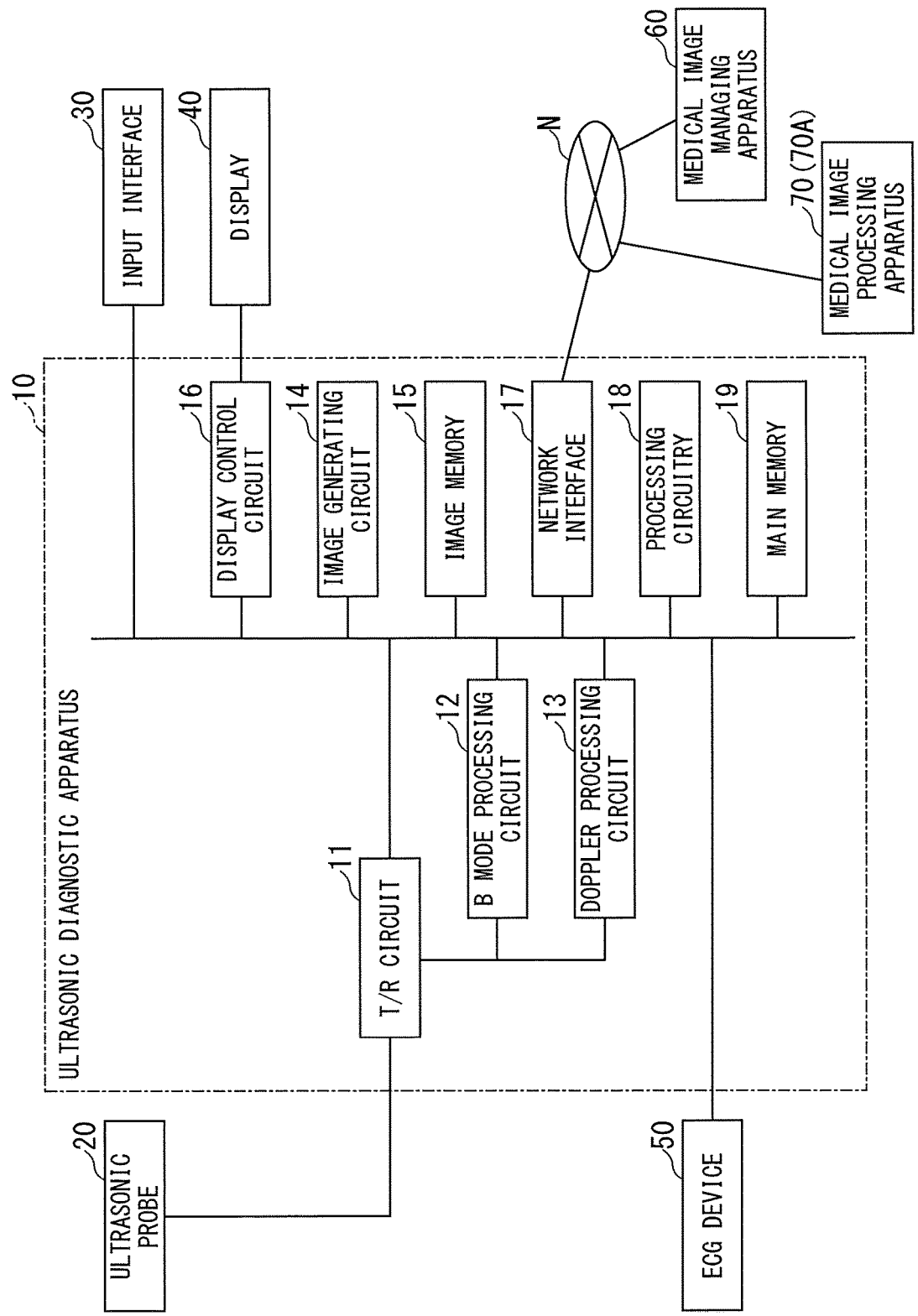
FIG. 1 is a schematic diagram showing a configuration of an ultrasonic diagnostic apparatus according to a first embodiment.

FIG. 1 is a schematic diagram showing a configuration of an ultrasonic diagnostic apparatus according to a first embodiment.

FIG. 1 shows an ultrasonic diagnostic apparatus 10 according to a first embodiment. FIG. 1 shows an ultrasonic probe 20, an input interface 30, a display 40, and an ECG device 50. It should be noted that a device in which at least one of the ultrasonic probe 20, the input interface 30, the display 40, and the ECG device 50 is added to the ultrasonic diagnostic apparatus 10 may be referred to as an ultrasonic diagnostic apparatus in some cases. In the following description, a case where all of the ultrasonic probe 20, the input interface 30, the display 40, and the ECG device 50 are provided outside the ultrasonic diagnostic apparatus 10 will be described.

The ultrasonic diagnostic apparatus 10 includes a transmitting/receiving (T/R) circuit 11, a B mode processing circuit 12, a Doppler processing circuit 13, an image generating circuit 14, an image memory 15, a display control circuit 16, a network interface 17, processing circuitry 18, and a main memory 19. The circuits 11 to 14 are configured by an application specific integrated circuit (ASIC) or the like. However, the present invention is not limited to this case, and all or a part of the functions of the circuits 11 to 14 may be realized by the processing circuitry 18 executing a program.

The T/R circuit 11 has a transmitting circuit and a receiving circuit (not shown). Under the control of the processing circuitry 18, the T/R circuit 11 controls transmission directivity and reception directivity in transmission and reception of ultrasonic waves. The case where the T/R circuit 11 is provided in the ultrasonic diagnostic apparatus 10 will be described, but the T/R circuit 11 may be provided in the ultrasonic probe 20, or may be provided in both of the ultrasonic diagnostic apparatus 10 and the ultrasonic probe 20. The T/R circuit 11 is an example of a T/R unit.

The transmitting circuit has a pulse generating circuit, a transmission delay circuit, a pulsar circuit and the like, and supplies a drive signal to ultrasonic transducers. The pulse generating circuit repeatedly generates a rate pulse for forming a transmission ultrasonic wave at a predetermined rate frequency. The transmission delay circuit converges the ultrasonic waves generated from the ultrasonic transducer of the ultrasonic probe 20 into a beam shape, and gives a delay time for each piezoelectric transducer necessary for determining the transmission directivity to each rate pulse generated by the pulse generating circuit. In addition, the pulsar circuit applies a drive pulse to the ultrasonic transducers at a timing based on the rate pulse. The transmission delay circuit arbitrarily adjusts the transmission direction of the ultrasonic beam transmitted from a piezoelectric transducer surface by changing the delay time given to each rate pulse.

The receiving circuit has an amplifier circuit, an analog to digital (A/D) converter, an adder, and the like, and receives the echo signal received by the ultrasonic transducers and performs various processes on the echo signal to generate echo data. The amplifier circuit amplifies the echo signal for each channel, and performs gain correction processing. The A/D converter A/D-converts the gain-corrected echo signal, and gives a delay time necessary for determining the reception directivity to the digital data. The adder adds the echo signal processed by the A/D converter to generate echo data. By the addition processing of the adder, the reflection component from the direction corresponding to the reception directivity of the echo signal is emphasized.

The B mode processing circuit 12 receives, under the control of the processing circuitry 18, the echo data from the receiving circuit, performs logarithmic amplification, envelope detection processing and the like, thereby generating data (two-dimensional or three-dimensional data) whose signal intensity is represented by brightness of luminance. This data is generally called B mode data. The B mode processing circuit 12 is an example of a B mode processing unit.

The Doppler processing circuit 13 frequency-analyzes, under the control of the processing circuitry 18, the phase information from the echo data from the receiving circuit, and extracts the blood flow or tissue due to the Doppler effect, thereby generating data (two-dimensional or three-dimensional data) obtained by extracting moving state information such as average speed, dispersion, power and the like for multiple points. This data is generally called Doppler data. The Doppler processing circuit 13 is an example of a Doppler processing unit.

The image generating circuit 14 generates, under the control of the processing circuitry 18, an ultrasonic image expressed in a predetermined luminance range as image data based on the echo signal received by the ultrasonic probe 20. For example, the image generating circuit 14 generates a B mode image in which the intensity of the reflected wave is expressed in luminance from the two-dimensional B mode data generated by the B mode processing circuit 12 as the ultrasonic image. Further, the image generating circuit 14 generates, as the ultrasonic image, a color Doppler image representing moving state information from the two-dimensional Doppler data generated by the Doppler processing circuit 13 such as an average velocity image, a dispersed image, a power image, or a combined image thereof. The image generating circuit 14 is an example of an image generating unit.

The image memory 15 includes memory cells in two axial directions per frame, and includes a two-dimensional memory which is a memory having the memory cells for frames. Under the control of the processing circuitry 18, the two-dimensional memory as the image memory 15 stores the ultrasonic image of one frame or the ultrasonic images frames generated by the image generating circuit 14 as two-dimensional image data. The image memory 15 is an example of a storage unit.

The image generating circuit 14 performs, under the control of the processing circuitry 18, three-dimensional reconstruction on the ultrasonic image arranged in the two-dimensional memory as the image memory 15, if necessary, by interpolation processing, thereby generating an ultrasonic image as volume data in a three-dimensional memory as the image memory 15. As an interpolation processing method, a known technique is used.

The image memory 15 may include a three-dimensional memory which is a memory having memory cells in three axial directions (X-axis, Y-axis, and Z-axis direction). The three-dimensional memory as the image memory 15 stores the ultrasonic image generated by the image generating circuit 14 as volume data under the control of the processing circuitry 18.

The display control circuit 16 includes a graphics processing unit (GPU), a Video RAM (VRAM), and the like. Under the control of the processing circuitry 18, the display control circuit 16 displays the ultrasonic image (for example, a live image), requested for display output from the processing circuitry 18, to the display 40. The display control circuit 16 is an example of a display control unit.

The network interface 17 implements various information communication protocols according to the form of the network. In accordance with these various protocols, the network interface 17 connects the ultrasonic diagnostic apparatus 10 and other devices such as the external medical image managing apparatus 60 and the medical image processing apparatus 70. As this connection, electrical connection or the like via an electronic network can be applied. In this embodiment, the electronic network means the whole information communication network using the telecommunication technology, and includes a local area network (LAN) of a wireless/wired hospital core and an internet network, a telephone communication network, an optical fiber communication network, a cable communication network, a satellite communication network, and the like.

Further, the network interface 17 may implement various protocols for non-contact wireless communication. In this case, for example, the ultrasonic diagnostic apparatus 10 can directly exchange data with the ultrasonic probe 20 without going through the network. The network interface 17 is an example of a network connection unit.

The processing circuitry 18 means an ASIC, a programmable logic device, etc. in addition to a dedicated or general purpose central processing unit (CPU), a microprocessor unit (MPU), or graphics processing unit (GPU). As the programmable logic device, for example, a simple programmable logic device (SPLD), a complex programmable logic device (CPLD), a field programmable gate array (FPGA).

Further, the processing circuitry 18 may be constituted by a single circuit or a combination of independent circuit elements. In the latter case, the main memory 19 may be provided individually for each circuit element, or a single main memory 19 may store programs corresponding to the functions of the circuit elements. The processing circuitry 18 is an example of a processing unit.

The main memory 19 is constituted by a semiconductor memory element such as a random access memory (RAM), a flash memory, a hard disk, an optical disk, or the like. The main memory 19 may be constituted by a portable medium such as a universal serial bus (USB) memory and a digital video disk (DVD). The main memory 19 stores various processing programs (including an OS (operating system) and the like besides the application program) used in the processing circuitry 18 and data necessary for executing the programs. In addition, the OS may include a graphical user interface (GUI) which allows the operator to frequently use graphics to display information on the display 40 to the operator and can perform basic operations by the input interface 30. The main memory 19 is an example of a storage unit.

The ultrasonic probe 20 includes microscopic transducers (piezoelectric elements) on the front surface portion, and transmits and receives ultrasonic waves to a region including a scan target, for example, a region including a lumen. Each transducer is an electroacustic transducer, and has a function of converting electric pulses into ultrasonic pulses at the time of transmission and converting reflected waves to electric signals (reception signals) at the time of reception. The ultrasonic probe 20 is configured to be small and lightweight, and is connected to the ultrasonic diagnostic apparatus 10 via a cable (or wireless communication).

The ultrasonic probe 20 is classified into types such as a linear type, a convex type, a sector type, etc., depending on a difference in scanning system. The ultrasonic probe 20 is classified into a 1D array probe in which transducers are arrayed in a one-dimensional (1D) manner in the azimuth direction, and a 2D array probe in which transducers are arrayed in two dimensions (2D) manner in the azimuth direction and in the elevation direction, depending on the array arrangement dimension. The 1D array probe includes a probe in which a small number of transducers are arranged in the elevation direction.

In this embodiment, when a 3D scan, that is, a volume scan is executed, the 2D array probe having a scan type such as the linear type, the convex type, the sector type, or the like is used as the ultrasonic probe 20. Alternatively, when the volume scan is executed, the 1D probe having a scan type such as the linear type, the convex type, the sector type and the like and having a mechanism that mechanically oscillates in the elevation direction is used as the ultrasonic probe 20. The latter probe is also called a mechanical 4D probe.

The input interface 30 includes an input device operable by an operator, and a circuit for inputting a signal from the input device. The input device may be a trackball, a switch, a mouse, a keyboard, a touch pad for performing an input operation by touching an operation surface, a touch screen in which a display screen and a touch pad are integrated, a non-contact input circuit using an optical sensor, an audio input circuit, and the like. When the input device is operated by the operator, the input interface 30 generates an input signal corresponding to the operation and outputs it to the processing circuitry 18. The input interface 30 is an example of an input unit.

The display 40 is constituted by a general display output device such as a liquid crystal display or an organic light emitting diode (OLED) display. The display 40 displays various kinds of information under the control of the processing circuitry 18. The display 40 is an example of a display unit.

The ECG device 50 measures an ECG signal as a signal representing a patient's heart (cardiac) phase. The ECG device 50 includes an ECG sensor and an ECG unit (not shown). The ECG sensor is attached to the patient's body surface and detects the patient's ECG signal as an electrical signal. The ECG unit subjects the ECG signal to various processing including digitization processing, and outputs the processed signal to the ultrasonic diagnostic apparatus 10. For example, a vector electrocardiograph is used as the ECG device 50.

Further, FIG. 1 shows the medical image managing apparatus 60 and the medical image processing apparatus 70 which are external devices of the ultrasonic diagnostic apparatus 10. The medical image managing apparatus 60 is, for example, a digital imaging and communications in medicine (DICOM) server, and is connected to a device such as the ultrasonic diagnostic apparatus 10 so that data can be transmitted and received via the network N. The medical image managing apparatus 60 manages a medical image such as an ultrasonic image generated by the ultrasonic diagnostic apparatus 10 as a DICOM file.

The medical image processing apparatus 70 is connected to devices such as the ultrasonic diagnostic apparatus 10 and the medical image management apparatus 60 so that data is transmitted and received via the network N. An Example of the medical image processing apparatus 70 includes a workstation that performs various image processing on the ultrasonic image generated by the ultrasonic diagnostic apparatus 10, a portable information processing terminal such as a tablet terminal. It should be noted that the medical image processing apparatus 70 is an offline apparatus and may be an apparatus capable of reading an ultrasonic image generated by the ultrasonic diagnostic apparatus 10 via a portable storage medium.

Subsequently, functions of the ultrasonic diagnostic apparatus 10 will be described.

Figure 2:
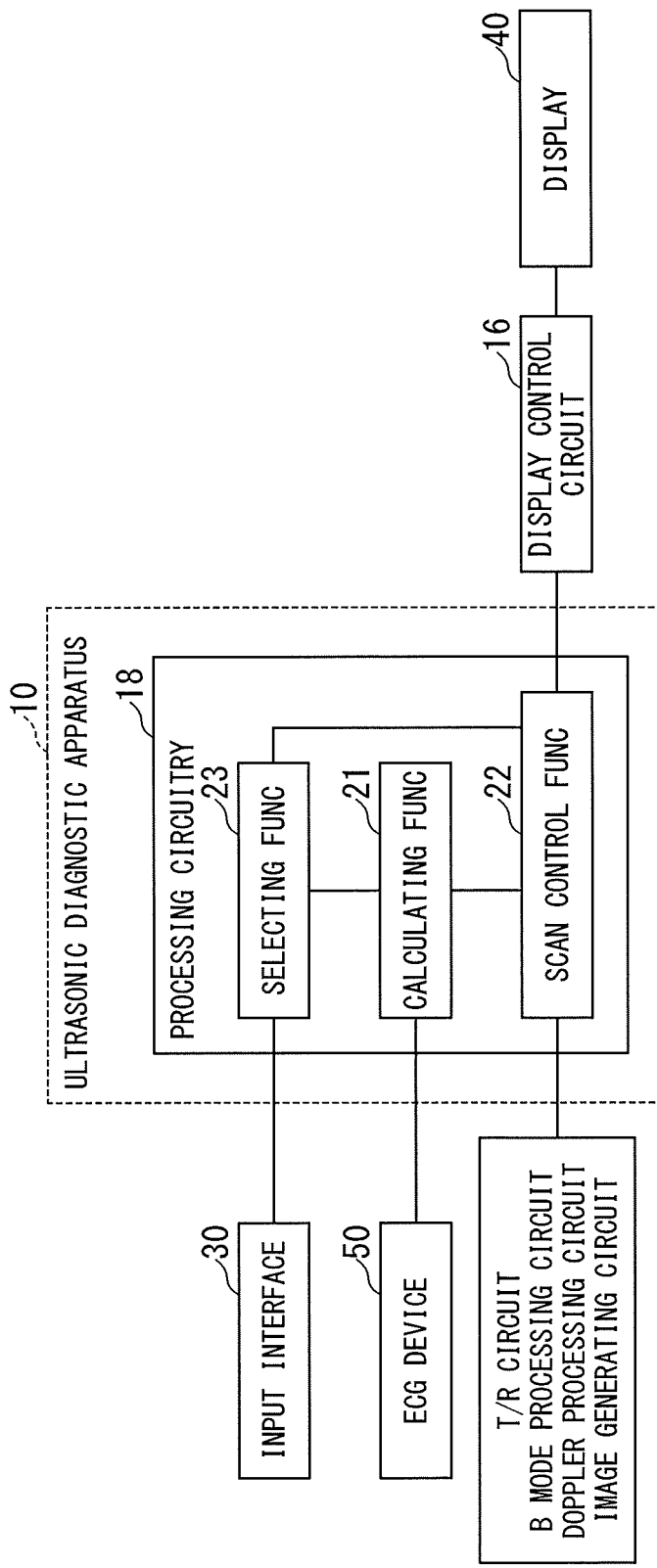
FIG. 2 is a block diagram showing functions of the ultrasonic diagnostic apparatus according to the first embodiment.

FIG. 2 is a block diagram showing functions of the ultrasonic diagnostic apparatus 10.

The processing circuitry 18 realizes a calculating function 21, a scan control function 22, and a selecting function 23 by reading and executing a program stored in the main memory 19 or directly incorporated in the processing circuitry 18. Hereinafter, the case where the functions 21 to 23 function as software will be described as an example. However, all or part of the functions 21 to 23 may be provided in the ultrasonic diagnostic apparatus 10 as a circuit or the like such as an ASIC.

The calculating function 21 has a function of detecting a specific heart phase (for example, R-wave) in a former heartbeat (for example, between R-wave and immediately before the next R-wave) and a specific heart phase in a subsequent latter heartbeat on the basis of the ECG signal, and a function of sequentially calculating a delay time from the specific heart phase in the latter heartbeat as a variable delay time on the basis of on a time interval between the specific heart phases in the former and latter heartbeats. In the embodiment, it is preferable to set the specific heart phase to an R-wave. The specific heart phase is not limited to the R-wave, and may be a P-wave, a Q-wave, an S-wave, a T-wave, or the like. The R-wave is easy to detect because the signal amplitude is large compared to the P-wave, the Q-wave, the S-wave, and the T-wave. The calculating function 21 is an example of a calculating unit.

The ECG signal used by the calculating function 21 is representatively based on the output of the ECG device 50, it is not limited to that case. For example, the ECG signal may be based on a waveform identified from a phonocardiogram (PCG) signal which is an output of a PCG device (not shown), or may be based on a waveform identified from changes in ultrasonic images. In the embodiment, the case where the ECG signal is based on the output of the ECG device 50 will be described.

The scan control function 22 has a function of generating an ultrasonic image (for example, a live image) by controlling the T/R circuit 11, the B mode processing circuit 12, the Doppler processing circuit 13, the image generating circuit 14 and the like to execute an ECG gated scan using the ultrasonic probe 20. The scan control function 22 controls the ultrasonic probe 20 to start the ECG gated scan at a timing when the delay time sequentially calculated by the calculation function 21 has elapsed from the specific heart phase (for example, R-wave) in the latter heartbeat. The scan control function 22 is an example of a scan control unit.

When the delay time from the R-wave which is the specific heart phase is set to "0" and when scanning is performed in synchronization with the R-wave, the scan control function 22 generates a color Doppler image to present an image or the like to the operator, which is used to diagnose regurgitation in mitral atresia. When the delay time from the R-wave is set and when scanning is performed in synchronization with the T-wave, the scan control function 22 generates a color Doppler image to present an image or the like to the operator, which is used to diagnose regurgitation in aortic valve atresia.

The selecting function 23 has a function of selecting a sequential calculation mode in which the delay time is sequentially calculated by the calculating function 21 or a fixed mode in which the fixed delay time is preset without using the calculating function 21. In the case of the sequential calculation mode as described above, the calculating function 21 sequentially calculates the delay time. Then, the scan control function 22 controls the ultrasonic probe 20 to start the scan at a timing when the delay time sequentially calculated has elapsed from the specific heart phase. On the other hand, in the case of the fixed mode, the scan control function 22 controls the ultrasonic probe 20 in all heartbeats to start the scan at a timing when a fixed delay time has elapsed from the specific heart phase. The selecting function 23 is an example of a selecting unit.

The details of the functions 21 to 23 will be described with reference to FIGS. 3 to 7.

Subsequently, an operation of the ultrasonic diagnostic apparatus 10 will be described.

Figure 3:
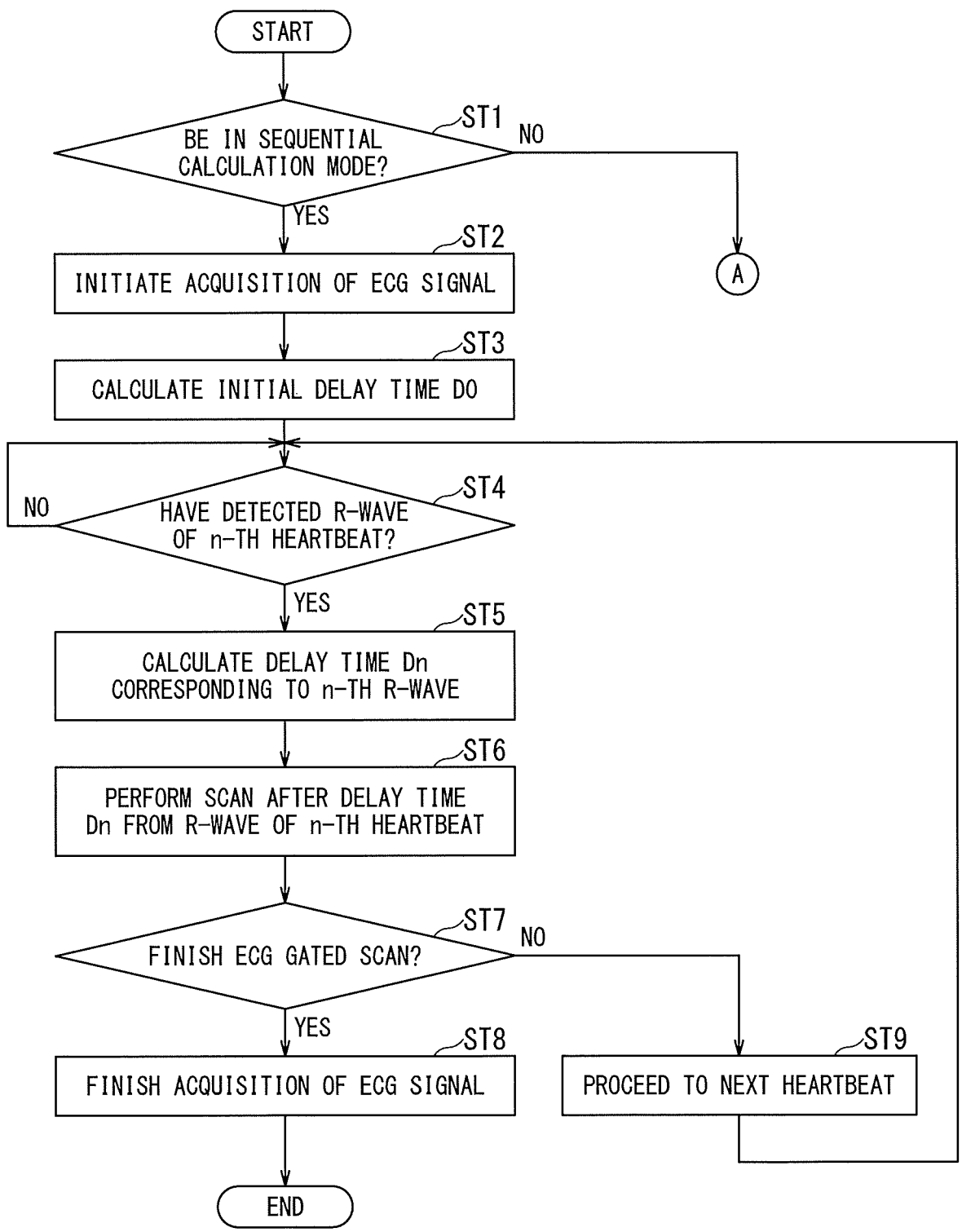
FIG. 3 is a diagram showing an operation of the ultrasonic diagnostic apparatus according to the first embodiment as a flowchart.
Figure 4:
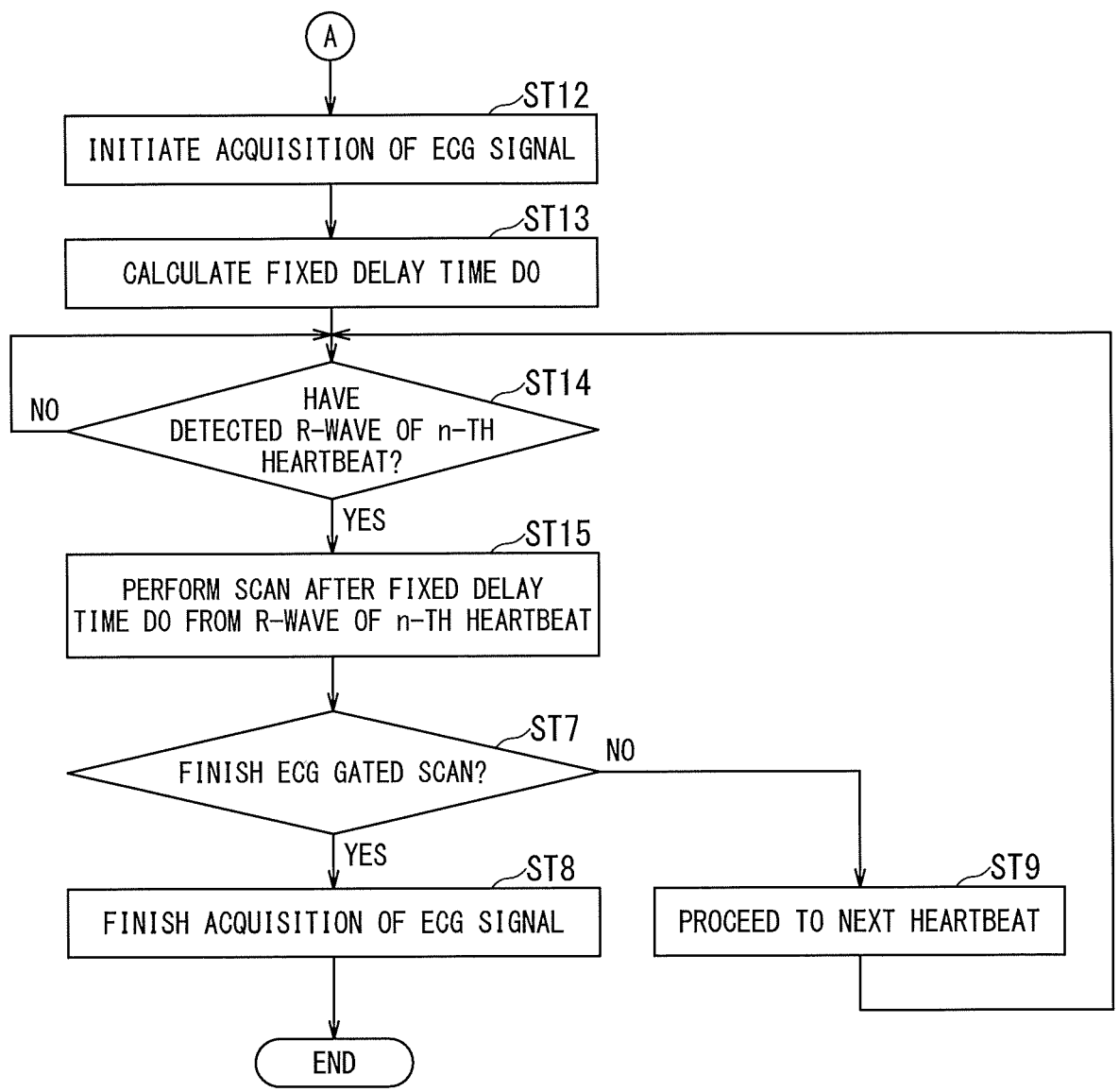
FIG. 4 is a diagram showing an operation of the ultrasonic diagnostic apparatus according to the first embodiment as a flowchart.

Each of FIGS. 3 and 4 is a diagram showing an operation of the ultrasonic diagnostic apparatus 10 as a flowchart. In FIGS. 3 and 4, reference numerals with numbers attached to "ST" indicate steps in the flowchart. In FIG. 4, the same steps as the steps shown in FIG. 3 are given the same reference numerals, so the description is omitted.

The selecting function 23 determines whether or not it is in a sequential calculation mode in which the delay time is sequentially calculated (step ST1). For example, according to the operation of the operator via the input interface 30, the selecting function 23 determines whether it is in the sequential calculation mode or the fixed mode.

If it is determined as "YES" in step ST1, that is, if it is determined in the sequential calculation mode, the calculating function 21 controls the ECG device 50 according to an instruction from the operator via the input interface 30 to initiate acquisition of an ECG signal (step ST2), so an ECG gated scan is initiated. The calculating function 21 calculates, when specific heartbeat phases such as R-waves are detected in heartbeats, an initial delay time (synonymous with "fixed delay time") D0 based on RR intervals in the heartbeats (step ST3).

The calculating function 21 determines whether the R-wave of the n-th heartbeat has been detected (step ST4). If it is determined as "NO" in step ST4, that is, if it is determined that the R-wave of the n-th heartbeat has not been detected, the calculating function 21 stands by until the R-wave of the n-th heartbeat has been detected.

If it is determined as "YES" in step ST4, that is, if the R-wave of the n-th heartbeat has been detected, the calculating function 21 calculates a delay time Dn corresponding to the R-wave of the n-th heartbeat (step ST5). In step ST5, the calculating function 21 calculates the delay time Dn from the R-wave of the n-th heartbeat on the basis of an interval between the R-wave in the (n−1)-th heartbeat and the R-wave of the n-th heartbeat, that is, RR interval.

After step ST5, the scan control function 22 controls the ultrasonic probe 20 and the like to initial a scan at the timing when the delay time Dn calculated in step ST5 has elapsed from the R-wave of the n-th heartbeat, thereby performs the scan (step ST6). The scan control function 22 is able to display the ultrasonic image generated by the scan performed in step ST6 to the display 40 as a live image, or to store the ultrasonic image in the image memory 15.

The scan control function 22 determines whether to finish the ECG gated scan (step ST7). For example, the scan control function 22 determines whether to finish the ECG gated scan according to the operation of the operator via the input interface 30. If it is determined as "YES" in step ST7, that is, if it is determined that the ECG gated scan is to be finished, the calculating function 21 controls the ECG device 50 to finish the acquisition of the ECG signal initialed in step ST2 (step ST8), then the ECG gated scan is finished.

If it is determined as "NO" in step ST7, that is, if it is determined that the ECG gated scan is not to be finished, the calculation function 21 proceeds to a next heartbeat (step ST9).

The ultrasonic diagnostic apparatus 10 repeats the operations of steps ST4 to ST6 in multiple heartbeats, and performs a scan using a variable delay time while sequentially calculating the variable delay time. In this embodiment, the significance of sequentially calculating the variable delay time will be described with reference to FIGS. 5 and 6.

Each of FIGS. 5A to 5C is a diagram showing an ECG waveform and a scan timing when the fixed delay time is adopted. FIG. 5A shows an ECG waveform and a scan timing when the RR interval is constant. FIG. 5B shows an ECG waveform and a scan timing when the RR interval is gradually shortened as compared with FIG. 5A. FIG. 5C shows an ECG waveform and the scan timing when the RR interval is gradually extended compared with FIG. 5A.

As shown in FIG. 5A, a fixed delay time D0 from the R-wave is set based on the initial RR interval so that the scan is initiated from a predetermined heartbeat phase in the ECG signal, for example, the T-wave. When the RR interval is stable, the scan initiates approximately from the T-wave even though the fixed delay time D0 is adopted.

However, as shown in FIG. 5B, when the fixed delay time D0 is adopted when the RR interval is gradually shortened, the RT interval is shortened. Then, as shown in FIG. 5B, the start of the scan gradually deviates from the T-wave, and the scan is unintentionally initiated after the T-wave. Further, as shown in FIG. 5C, when the fixed delay time D0 is adopted when the RR interval is gradually extended, the RT interval is extended. Then, as shown in FIG. 5C, the start of the scan gradually deviates from the T-wave, and the scan is unintentionally initiated before the T-wave.

If the delay time from the R-wave cannot be varied according to the variation of the RR interval, the scan cannot be initiated according to the actual movement of the living body. Therefore, it is considered to correct the delay time automatically according to the fluctuation of the RR interval and to sequentially calculate the variable delay time.

Each of FIGS. 6A and 6B is a diagram showing an ECG waveform and a scan timing when the variable delay time is adopted. FIG. 6A shows an ECG waveform and a scan timing when the RR interval is gradually shortened as compared with FIG. 5A. FIG. 6B shows an ECG waveform and a scan timing when the RR interval is gradually extended as compared with FIG. 5A.

As shown in FIG. 6A, when the RR interval is gradually shortened, the variable delay time Dn based on the RR interval between two (n−1)-th and n-th heartbeats is calculated. For example, the variable delay time D2 of the 2nd heartbeat is calculated from the RR interval based on the R-wave of the 1st heartbeat and the R-wave of the 2nd heartbeat. Therefore, as shown in FIG. 6A, even when the RR interval is gradually shortened, the shift (delay) from the T-wave at the start of the scan is minimized.

Further, as shown in FIG. 6B, when the RR interval is gradually extended, the variable delay time Dn based on the RR interval between two (n−1)-th and n-th heartbeats is adopted. For example, the variable delay time D2 of the 2nd heartbeat is calculated from the RR interval based on the R-wave of the 1st heartbeat and the R-wave of the 2nd heartbeat. Therefore, as shown in FIG. 6B, even when the RR interval gradually extended, the shift (early) from the T-wave at the start of the scan is minimized.

Here, a method of calculating the variable delay time will be described.

The initial delay time D0 is "Tds", and the RR interval in that case is "RRs". When the ultrasonic diagnostic apparatus 10 calculates the variable delay time, the delay time Tds and the RR interval RRs are used. In addition, the variable delay time is "Tdc".

First of all, assuming that a QT interval is "QT", a correction value QTc of the QT interval can be calculated using the following known Bazett correction equation (1), Fridericia correction equation (2), Hodges correction equation (3), or Framingham correction equation (4). The variation of RR interval affects the QT interval. That is, the longer the RR interval, the longer the QT interval, and the shorter the RR interval, the shorter the QT interval.

$$QTc = \frac{QT}{\sqrt{RR}} \quad (1)$$

$$QTc = \frac{QT}{\sqrt[3]{RR}} \quad (2)$$

$$QTc = QT + 105\left(\frac{1}{RR-1}\right) \quad (3)$$

$$QTc = QT - 0.154(1 - RR) \quad (4)$$

Consider a case where the above equation (4) is modified for the calculation equation for acquiring the variable delay time Tdc. It should be noted that the calculation equation for acquiring the variable delay time Tdc is not limited to the case where the equation (4) is deformed. The equation for acquiring the variable delay time Tdc can also be acquired by deforming any one of the above equations (1) to (3). The equation (4) is deformed into the following equation (5). Further, when it is considered that a coefficient C is considered equal to Td/QT and approximately equal to "1", it can be expressed as the following equation (6). This shows a variable value when the RR interval fluctuates from 1000 [ms] to RR. If the variable delay time Tdc is in "ms", there is no problem in considering the coefficient C is considered equal to "1".

$$QTc = QT - 0.154(1000 - RR)$$

$$QTc - QT = -0.154(1000 - RR)$$

$$Tdc = Td + \frac{Td(QTc - QT)}{QT} = Td - \frac{Td}{QT} \times 0.154(1000 - RR) \quad (5)$$

$$Tdc = Td - 0.154(1000 - RR) \quad (6)$$

Further, when the RR interval varies from "RRs" to "RR", it can be expressed by the following equation (7). In consideration of the fact that the coefficient C is equal to Td/QT in the following equation (7), it can be expressed as the following equation (8). According to the following equation (8), when the variable delay time Tdc is a unit smaller than "ms" (for example, "us"), it is possible to perform finer correction by adjusting the coefficient C.

$$Tdc = Tds + 0.154(1000 - RRs) = Tds + 0.154(RR - RRs) \quad (7)$$

$$Tdc = Tds + C \times 0.154(RR - RRs) \quad (13)$$

As shown in FIG. 6A, "RRs" with a short RR interval is 1500 [ms], and the initial delay time (Tds) is set as 400 [ms]. In this case, when the RR interval varies to 1000 [ms], the variable delay time Tdc is acquired as follows on the basis of the above equation (7).

$$Tdc = 400 + 0.154(1000 - 1500) = 323$$

A delay of 323 [ms] of the variable delay time (Tdc) from the R-wave is made to advance the timing of the scan initiating. Thereby, it is possible to initiate the scan at the timing of the T-wave according to the movement of the living body.

As shown in FIG. 6B, "RRs" with an extended RR interval is 1500 [ms], and the initial delay time (Tds) is set as 400 [ms]. In this case, when the RR interval varies to 2000 [ms], the variable delay time Tdc is acquired as follows on the basis of the above equation (7).

$$Tdc = 400 + 0.154(2000 - 1500) = 477$$

A delay of 477 [ms] of the variable delay time (Tdc) from the R-wave is made to delay the timing of the scan initiating. Thereby, it is possible to initiate the scan at the timing of the T-wave according to the movement of the living body. An example of the relationship between the RR interval (RR) and the variable delay time (Tdc) is shown in FIG. 7, when the RR interval (RRs) is 1500 [ms] and the initial delay time (Tds) is 400 [ms]. It should be noted that the case of calculating the variable delay time (Tdc) based on the QT interval has been described, the present invention is not limited to this case. For example, the variable delay time (Tdc) may be calculated based on the RT interval.

Returning to the description of FIG. 3, if it is determined as "NO" in step ST1, that is, it is determined in the fixed mode, the process proceeds to FIG. 4. The calculating function 21 controls the ECG device 50 according to an instruction from the operator via the input interface 30 to initiate acquisition of an ECG signal (step ST12), so an ECG gated scan is initiated. The calculating function 21 calculates, when R-waves are detected in heartbeats, a fixed delay time D0 based on the RR intervals in the heartbeats (step ST13).

The calculating function 21 determines whether the R-wave of the n-th heartbeat has been detected (step ST14). If it is determined as "NO" in step ST14, that is, if it is determined that the R-wave of the n-th heartbeat has not been detected, the calculating function 21 stands by until the R-wave of the n-th heartbeat has been detected.

If it is determined as "YES" in step ST14, that is, if the R-wave of the n-th heartbeat has been detected, the scan control function 22 controls the ultrasonic probe 20 and the like to initial a scan at the timing when the fixed delay time D0 calculated in step ST13 has elapsed from the R-wave of the n-th heartbeat, thereby performs the scan (step ST15). That is, the ultrasonic diagnostic apparatus 10 performs the scan using the fixed delay time D0 in all the heartbeats by repeating the operation of steps ST14 to ST5 in heartbeats (see FIG. 5).

According to the ultrasonic diagnostic apparatus 10, the delay time from the specific heart phase is sequentially calculated according to each of different intervals (for example, RR interval) of the heart phase, so it is possible to acquire the ultrasonic image according to change in movement of the heart. In particular, if stress echo is applied which places a load on the patient, the sequential calculation of the delay time is more effective since the RR interval fluctuates. In addition, since the RR interval changes similarly when the patient has an arrhythmia, sequential calculation of the delay time is more effective.

2. Modified Example

As described with reference to FIGS. 6A and 6B, the calculating function 21 calculates the variable delay time Dn based on the RR interval between the two (n−1)-th and n-th heartbeats. As a result, even if the RR interval is gradually shortened, or even if the RR interval is gradually extended, the deviation from the T-wave at the scan initiating is minimized.

In addition, the case where the patient has an arrhythmia includes not only a case where the pulse strikes slowly, and a case where the pulse strikes fast, but also a case where the pulse strikes irregularly. In this embodiment, the case where the pulse strikes irregularly will be described as an example.

Each of FIGS. 8A and 8B is a diagram showing an ECG waveform and a scan timing when the variable delay time is adopted in the ultrasonic diagnostic apparatus according to the first embodiment.

FIG. 8A shows an ECG waveform in the case where one heartbeat to be present between the 1st heartbeat and the 2nd heartbeat is absence. In the case of such arrhythmia, the variable delay time D2 is calculated based on the RR interval between 1st and 2nd heartbeats. Then, the variable delay time D2 may be set to be long due to the influence of the one beat absent (shown in FIG. 8A).

Therefore, the calculating function 21 sets a delay time Dn in n-th heartbeat to be the same as a delay time Dn-1 in (n−1)-th heartbeat, when a specific heart phase (for example, R-wave) in the n-th heartbeat does not appear even if a predetermined time Un-1 elapses after the specific heart phase in the (n−1)-th heartbeat. For example, as shown in FIG. 8B, the calculating function 21 sets a delay time D2 in 2nd heartbeat to be the same as a delay time D1 in 1st heartbeat, when R-wave in the 2nd heartbeat does not appear even if a predetermined time U1 elapses after the R-wave in the 1st heartbeat.

In this embodiment, the calculating function 21 calculates the predetermined time Un at the n-th heartbeat from an average time W of the predetermined number of RR intervals in the same patient. For example, the calculating function 21 sets the predetermined time Un as a time acquired by adding a margin time Mn to the average time W (Un=W+Mn). The scan of a patient with arrhythmia is assumed, so the margin time Mn is not uniquely determined, but the calculating function 21 may set the margin time Mn as the delay time Dn (Un=W+Dn). For example, as shown in FIG. 8B, the calculating function 21 sets a predetermined time U1 in the 1st heartbeat as a time acquired by adding the delay time D1 to the average time W. This is because the delay time Dn is one indicator which represents the time lag of each heartbeat.

It should be noted that the margin time Mn is not limited to the case of the delay time Dn. The margin time Mn may be a time acquired by multiplying the delay time Dn by a predetermined coefficient j (j=0.9, 1.1 or the like) (Un=W+Dn×j). In addition, the predetermined time Un may be a time acquired by multiplying the average time W by a coefficient k (k=1.1 or the like) set in advance regardless of "n" (Un=W×k).

The calculating function 21 may acquire the predetermined time Un at the n-th heartbeat from other than the average time W. For example, the predetermined time Un may be a constant time set in advance regardless of "n".

As described above, it is possible to correct the delay time lag which may occur in the case of an arrhythmia in which pulses beat irregularly as shown in FIG. 8A.

3. Second Embodiment

The technical concept shown in the first embodiment described above may be applied to an external apparatus of the ultrasonic diagnostic apparatus 10, for example, a medical image processing apparatus 70A (shown in FIG. 1).

FIG. 9 is a schematic view showing a configuration of a medical image processing apparatus according to a second embodiment.

FIG. 9 shows a medical image processing apparatus 70A according to a second embodiment. The medical image processing apparatus 70A includes processing circuitry 61A, a memory 62, an input interface 63, a display control circuit 64, and a display 65. The processing circuitry 61A, the memory 62, the input interface 63, the display control circuit 64, and the display 65 are equivalent to the configuration of the processing circuitry 18, the main memory 19, the input interface 30, the display control circuit 16, and the display 40 shown in FIG. 1 respectively, so the description thereof is omitted.

The processing circuitry 61A implements the calculating function 21A and the reconstructing function 24A by reading and executing a program stored in the memory 62 or incorporated directly into the processing circuitry 61A. Hereinafter, the case where the functions 21A and 24A function as software will be described as an example. However, all or part of the functions 21A and 24A may be provided in the medical image processing apparatus 70A as a circuit or the like such as an ASIC.

The memory 62 stores, in advance, multiple sub-volume data (v11 to v46 shown in FIG. 11) generated as data for the triggered scan span T by the ultrasonic diagnostic apparatus.

Sub-volume data is data in which data is arranged in a sub-volume. Also, multiple spatially adjacent sub-volume data forms full-volume data.

FIG. 10 is a diagram showing a relationship between multiple sub volume data and full volume data.

FIG. 10 shows four sub-volume areas v1, v2, v3 and v4, and a full volume area V (=v1+v2+v3+v4) constituted by the four sub-volume areas v1 to v4. The generation of six sub-volume data within one heartbeat time span T is performed by performing an ECG gated scan based on a fixed delay time by the ultrasonic diagnostic apparatus for each of the four sub-volume regions v1 to v4 (See FIG. 11). In other words, a total of 24 pieces of sub-volume data are acquired by performing the ECG gated scan based on a fixed delay time by the ultrasonic diagnostic apparatus (see FIG. 11).

Returning to the explanation of FIG. 9, the calculating function 21A has a function of detecting a specific heart phase (for example, R-wave) in a former heartbeat and a specific heart phase in a subsequent latter heartbeat on the basis of the ECG signal corresponding to the sub-volume data stored in memory 62, and a function of calculating a delay time from the specific heart phase in the latter heartbeat as a variable delay time on the basis of on a time interval between the specific heart phases in the former and latter heartbeats. In the embodiment, it is preferable to set the specific heart phase to an R-wave. The specific heart phase is not limited to the R-wave, and may be a P-wave, a Q-wave, an S-wave, a T-wave, or the like. The R-wave is easy to detect because the signal amplitude is large compared to the P-wave, the Q-wave, the S-wave, and the T-wave. The calculating function 21A is an example of a calculating unit.

The reconstructing function 24A has a function of acquiring a heart phase of each sub-volume data stored in the memory 62 on the basis of the specific heart phase and the variable delay time calculated by the calculating function 21A, and a function of generating the full-volume data by correlating the multiple sub-volume data by the acquired heart phase based on the variable delay time. The reconstructing function 24A is an example of a reconstructing unit.

FIG. 11 is a diagram showing an example of multiple sub-volume data.

FIG. 11 shows six sub-volume data corresponding to the four sub-volume areas v1 to v4, respectively. In the ECG gated scan, six sub-volume data v11 to v16 are sequentially generated by six scans after the fixed delay time has elapsed from the R-wave within the same heartbeat. In the next heartbeat, six sub-volume data v21 to v26 are sequentially generated by six scans after the fixed delay time has elapsed from the R-wave. Similarly, six sub-volume data v31 to v36 and six sub-volume data v41 to v46 are generated.

The calculating function 21A is able to calculate the time, corresponding to each sub volume, from the lapse of the variable delay time on the basis of the ECG signal associated with each sub-volume. Therefore, the reconstructing function 24A uses the variable delay time instead of the fixed delay time, and extracts, one by one from the sub-volume areas v1 to v4, sub-volume data in which the times from the lapse of the variable delay time substantially coincide. Thereby, it is possible to generate the full-volume data. As a result, the reconstructing function 24A is able to spatially join sub-volume data according to the actual movement of the heart.

According to the medical image processing apparatus 70A, the delay time from the specific heart phase is calculated according to each of different intervals (for example, RR interval) of the heart phase, so it is possible to acquire the volume data based on the multiple sub-volume data corresponding to change in heart movement.

According to at least one of the embodiments described above, it is possible to acquire ultrasonic data according to the change in heart movement.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An ultrasonic diagnostic apparatus, comprising:
an electrocardiogram (ECG) device configured to output an ECG signal from a patient;
processing circuitry configured to:
detect R-waves from the ECG signal,
determine a time of an initial RR interval as a time between two adjacent R-waves of the ECG signal,
set an initial delay time of the initial RR interval,
determine a plurality of times of each of a plurality of detected subsequent RR intervals after the initial RR interval,
calculate, for each of the plurality of detected subsequent RR intervals, a coefficient based on a time difference between each of the plurality of detected subsequent RR intervals and the initial RR interval,
calculate, for each of the plurality of detected subsequent RR intervals, a non-fixed delay time by adding the calculated coefficient to the initial delay time, thereby sequentially calculating a plurality of the non-fixed delay times for each of the plurality of detected subsequent RR intervals; and
an ultrasonic probe configured to initiate ultrasonic scans for each of the plurality of detected subsequent RR intervals at a timing when the calculated non-fixed delay time is elapsed, thereby sequentially initiating a plurality of the ultrasonic scans for each of the plurality of detected subsequent RR intervals.

2. The ultrasonic diagnostic apparatus according to claim 1, wherein the processing circuitry is further configured to set the non-fixed delay time in each of the plurality of detected subsequent RR intervals to be the a same as a delay time in the initial RR interval, when the R-wave of the initial RR interval does not appear even if when a predetermined time elapses after the R-wave of the initial RR interval.

3. The ultrasonic diagnostic apparatus according to claim 2, wherein the processing circuitry is further configured to set the predetermined time as a time acquired by adding a margin time to an average time of a plurality predetermined RR intervals.

4. The ultrasonic diagnostic apparatus according to claim 3, wherein the processing circuitry is further configured to set the margin time as the non-fixed delay time, thereby setting the predetermined time as a time acquired by adding the non-fixed delay time to the average time of a plurality of predetermined RR intervals.

5. A method for controlling an ultrasonic scan, comprising:
outputting, by an electrocardiogram (ECG) device, an ECG signal from a patient, detecting, by processing circuitry, R-waves from the ECG signal,
determining, by processing circuitry, a time of an initial RR interval as a time between two adjacent R-waves of the ECG signal,
setting, by processing circuitry, an initial delay time of the initial RR interval,
determining, by processing circuitry, a plurality of times of each of a plurality of detected subsequent RR intervals after the initial RR interval,
calculating, by processing circuitry for each of the plurality of detected subsequent RR intervals, a coefficient based on a time difference between each of the plurality of detected subsequent RR intervals and the initial RR interval,
calculating, by processing circuitry for each of the plurality of detected subsequent RR intervals, a non-fixed delay time by adding the calculated coefficient to the initial delay time, thereby sequentially calculating a plurality of the non-fixed delay times in each of the plurality of detected subsequent RR intervals, and
initiating, by an ultrasonic probe, ultrasonic scans for each of the plurality of detected subsequent RR intervals at a timing when the calculated non-fixed delay time is elapsed, thereby sequentially initiating a plurality of the ultrasonic scans for each of the plurality of detected subsequent RR intervals.

\* \* \* \* \*